United States Patent [19]

Nakashima et al.

[11] Patent Number: 4,645,662

[45] Date of Patent: Feb. 24, 1987

[54] ORAL COMPOSITION

[75] Inventors: Syozi Nakashima, Hadano; Akinori Takahashi, Chigasaki; Nobuo Suganuma; Satoshi Ito, both of Narashino, all of Japan

[73] Assignee: Lion Corporation, Tokyo, Japan

[21] Appl. No.: 758,723

[22] Filed: Jul. 25, 1985

[30] Foreign Application Priority Data

Jul. 26, 1984 [JP] Japan ................................ 59-156309

[51] Int. Cl.⁴ ......................... A61K 7/16; A61K 7/18; A61K 7/22; A61K 7/24

[52] U.S. Cl. ....................................... 424/52; 424/48; 424/49; 424/50; 424/54; 424/55; 424/57; 424/58; 424/154; 424/157

[58] Field of Search ..................................... 424/48–58, 424/154, 157

[56] References Cited

U.S. PATENT DOCUMENTS

| | | |
|---|---|---|
| 2,550,207 | 4/1951 | Tainter .................................. 424/49 |
| 2,818,371 | 12/1957 | Wessinger ............................. 424/52 |
| 3,988,434 | 10/1976 | Schole et al. ......................... 424/54 |
| 4,011,309 | 3/1977 | Lutz ....................................... 424/49 |
| 4,042,680 | 8/1977 | Muhler et al. ........................ 424/55 |
| 4,108,979 | 8/1978 | Muhler et al. ........................ 424/49 |
| 4,108,981 | 8/1970 | Muhler et al. ........................ 424/55 |
| 4,146,605 | 3/1979 | Ritchey ................................. 424/49 |
| 4,146,607 | 3/1979 | Ritchey ................................. 424/54 |
| 4,153,732 | 5/1979 | Muhler et al. ........................ 426/72 |
| 4,296,094 | 10/1981 | Matsushima et al. ................ 424/49 |
| 4,335,102 | 6/1982 | Nakashima et al. ................. 424/52 |
| 4,538,990 | 9/1985 | Pashley ................................. 106/35 |

*Primary Examiner*—Shep K. Rose
*Attorney, Agent, or Firm*—Birch, Stewart, Kolasch and Birch

[57] ABSTRACT

An oral composition for preventing and remedying dentinal hypersensitivity which comprises containing therein aluminum and a carboxylate compound in solubilized state, with the molar ratio of the carboxylate compound to aluminum being lower than 6, and having a pH value higher than 5.

44 Claims, No Drawings

ORAL COMPOSITION

BACKGROUND OF THE INVENTION

1. Field of the Invention:

The present invention relates to an oral composition to effectively prevent and remedy dentinal hypersensitivity.

2. Description of the Prior Art:

Dentinal hypersensitivity is a name of disease given after the clinical symptoms. It causes acute transient pain when the dentin receives thermal, chemical, mechanical, physicochemical, electrical, and other external stimuli, because the dentin is exposed due to the loss of enamel or cement which results from dental caries, attrition, abrasion, or recession of gingiva. The pain is induced when the patient eats a sweet food or sour fruit, or drinks cold water, or brushes his teeth. This pain adversely affects one's eating habits and oral hygiene.

The following two theories are main the hypotheses for the transmission mechanism of pain-producing stimulus in dentinal hypersensitivity.

(A) Transducer Theory . . . Odontoblasts or their processes existing in dentinal tubules work as a receptor for stimulus to transmit its information to nerve fibers in the pulp.

(B) Hydrodynamic Theory . . . Stimulus applied to dentinal surface causes the movement of dentinal fluid which then stimulates free nerve endings existing in the dentin-pulp region, thereby causing pain.

At present, the latter theory (hydrodynamic theory) is predominant with the support by M. Bränström (Calorinsca Institute), Pashley (Georgia Pharmaceutical College), and B. Matthew (Bristol University). A human molar dentin has 20,000 to 30,000 dentinal tubules per mm$^2$ (about 1.0 $\mu$m in diameter) at the enamel side and 30,000 to 40,000 tubules per mm$^2$ (about 3.0 $\mu$m in diameter) at the pulp side. When the enamel or cement is lost, the external stimuli applied to the surface of the exposed dentin cause the fluid flow in the dentinal tubules, thereby exciting the sensory nerve in the dental pulp, and then giving a pain.

The effective means to relieve, eliminate, or prevent the dentinal hypersensitivity is to close or block the orifice of the dentinal tubules, thereby suppressing or inhibiting the transmission of stimuli.

Studies of therapeutic agents for improving dentinal hypersensitivity have been carried out from considerably old times. Grossman, L. E. (1935) listed six ideal prerequisites for the therapeutic agent for this disease.

(1) Non-irritant to the pulp
(2) Relatively painless upon application
(3) Easily applied
(4) Rapid in action
(5) Effective for a long time
(6) without staining effects It is said that there are no methods meeting all these prerequisites at present.

According to the aforementioned hypotheses for the stimulus transmission mechanism, the currently performed therapeutics are roughly categorized into the following two groups.

(I) The methods of neurophysiologically desensitizing the stimulus-receptors (odontblasts and nerve fibers) by means of medicines.

(II) The methods of inhibiting the transmission of stimulus to free nerve endings by suppressing the movement of dentinal fluid (according to the hydrodynamic theory).

The tangible methods belonging to the category (I) include those in which various kinds of cauteries and medicines having the effect of denaturing and coagulating protein (such as formalin, paraformaldehyde, zinc chloride, strontium chloride, carbonates and silver compounds) are applied. The tangible methods belonging to the category (II) include the methods of occluding tubular orifices (with various kinds of dental cements, adhesive resins and periodontal surgical packs), the methods of constricting dentinal tubules by depositing calcium salts or water-insoluble salts (such as various kinds of fluorides, strontium chloride, citrates, mixture consisting of potassium ferrocyanide and zinc chloride and silver compounds) around tubular orifices, and the methods of constricting dentinal tubules by accelerating the formation of secondary dentin (by means of calcium hydroxide, paraformaldehyde, etc.). These methods of various kinds are applied according to the symptoms of patient suffering dentinal hypersensitivity. However, as seen from the six prerequisites determined by Grossman, all of these methods have various disadvantages and problems which should be improved such as a complicate technique, a possibility of causing damage to oral tissue, a small measure of success and staining effects.

Heretofore, there are proposed several oral compositions intended for the prevention or treatment of dentinal hypersensitivity. However, most of them are not intended for occlusion of tubular orifices; in other words, they are not designed to prevent the nerve from being stimulated by the movement of the dentinal tubule fluid, but are designed for performing indirect prevention and treatment through desensitizing the nerve.

For example, the U.S. Pat. No. 3,514,513 discloses the use of aluminum chlorohydroallantoinate as a therapeutic ingredient for dentinal hypersensitivity. However, aluminum chlorohydroallantoinate is not so effective, as shown in the Examples shown below, when evaluated by using the split chamber device for measuring the dentin hydrauric conductance described by Pashley, D. H. (J. Dent. Res., 60(3)686–698, 1981) which the present inventors accepted to examine the effect on the occlusion of tubular orifices. This method is suitable as an evaluation of the agents having the ability to reduce the dentin permeability.

There is also known an oral composition which contains an aluminum compound and fluorine compound together for the prevention of dental calculus (U.S. Pat. No. 4,146,605). This patent discloses that the composition can be incorporated with citric acid or lactic acid. The composition containing such an acid has the pH value lower than 4.5. The low pH is not effective for the occlusion of tubular orifices, as shown in the experimental examples that follow.

There is disclosed in U.S. Pat. No. 3,651,207 a mouthwash containing aluminum dihydroxyallantoinate, citric acid, tartaric acid, and sodium hydrogenphosphate. This mouthwash is not effective for dentinal hypersensitivity because the content of aluminum is low relative to the content of citric acid and tartaric acid.

SUMMARY OF THE INVENTION

Accordingly, it is an object of the present invention to provide an oral composition which is effective on the occlusion of tubular orifices and effectively prevents and remedies dentinal hypersensitivity.

More particularly, the present inventors have attempted to develop an oral composition which requires only a simple technique and enables dentinal hypersensitivity to be prevented and treated without causing any damage and without staining teeth. When searching for effective components, the method of closing and blocking the tubular orifices of exposed dentin was adopted according to the hydrodynamic theory of the aforementioned two hypotheses for the stimulus transmission mechanism. As a result, it was found that the constriction or occlusion of tubular orifices can be effectively accomplished and consequently the dentinal hypersensitivity can be effectively prevented and remedied if the oral composition contains aluminum and a carboxylate compound in a solubilized state with the molar ratio of the carboxylate compound to aluminum being lower than 6 and the pH of the composition being higher than 5.

Therefore, the present invention provides an oral composition for preventing and remedying dentinal hypersensitivity containing aluminum and a carboxylate compound in a solubilized state, characterized in that the molar ratio of a carboxylate compound to aluminum is lower than 6 and the composition has a pH value higher than 5.

The above and other objects, features and advantages of the present invention will be more apparent from the following description.

DETAILED DESCRIPTION OF THE INVENTION

The oral composition of this invention is used in the form of toothpaste, toothpowder, ointment (liquid or gel), mouthwash, dental floss, oral band, etc. The oral composition contains aluminum and a carboxylate compound in solubilized state, with the content of aluminum being 1 mol and the content of the carboxylate compound being 6 mol or less, and has a pH value of 5 or above. "In solubilized state" means either the case in which the above-mentioned ingredients are solubilized in the oral composition and the case in which the ingredients are present partly in the form of precipitates. The above-mentioned ingredients may be in the form of dissolved free ions or in the form of dissolved chelate.

The oral composition may be incorporated with aluminum and a carboxylate compound in the form of aluminum carboxylate or with an aluminum compound which does not containing carboxyl group and a carboxylic acid or a salt thereof separately. The aluminum carboxylate includes aluminum monocarboxylates (e.g., aluminum lactate, aluminum gluconate, and aluminum glycolate), aluminum dicarboxylates (e.g., aluminum malonate, aluminum glutarate, aluminum malate, and aluminum tartrate), and aluminum tricarboxylates (e.g., aluminum citrate). They may be normal salts, basic salts, or abnormal salts. In addition to the above-mentioned aluminum carboxylates, the aluminum compounds including $Al(NH_4)(SO_4)_2$, $AlCl_3$, $AlF_3$, $[Al(OH)_2Cl]_x$, $Al(NO_3)_3$, $KAl(SO_4)_2$, $NaAl(SO_4)_2$, $Al_2(SO_4)_3$, $Al(SiF_6)_3$ and the like can be used. The carboxylic acid and salt thereof include the mono- di-, and tricarboxylic acids and alkali metal salts thereof. Two or more of these compounds may be used in combination in this invention.

Preferable among the above-mentioned carboxyl group-containing compounds are those compounds having both carboxyl and hydroxyl groups, particularly monocarboxylate compounds having at least one hydroxyl group such as lactic acid, glycolic acid, and gluconic acid, and salts thereof.

According to this invention, 1 mol of aluminum and less than 6 mol, preferably 0.1 to 6 mol, of the carboxylate compound are incorporated in the solubilized state. The molar amount of the carboxylate compound to aluminum may preferably vary depending on the basicity of the carboxylate compound. The preferred amount is 0.7 to 5 mol, particularly 1 to 4 mol, for a monocarboxylate compound, 0.2 to 2.5 mol, particularly 0.3 to 2 mol, for a dicarboxylate compound, and 0.1 to 2 mol, particularly 0.2 to 1.5 mol, for a tricarboxylate compound to 1 mol of aluminum.

The amount of aluminum is not specifically limited; but the preferred amount is such that the solubilized aluminum accounts for 0.01 to 10% by weight, particularly 0.1 to 5% by weight in the composition.

The oral composition of this invention may be incorporated with a water-soluble phosphoric acid compound in addition to aluminum and the carboxylate compound. It enhances the effect of preventing and remedying dentinal hypersensitivity.

Examples of the phosphoric acid compound include orthophosphoric acid, glycerophosphoric acid, pyrophosphoric acid, tripolyphosphoric acid, hexametaphosphoric acid, phytic acid, and ethane-1-hydroxy-1,1-diphosphonic acid, and sodium salt, potassium salt, and ammonium salt thereof. They may be used individually or in combination with one another. The oral composition contains the phosphoric acid compound in the dissolve state. The content of the phosphoric acid compound should be such that the solubilized portion accounts for 0.01 to 10% by weight, particularly 0.1 to 5% by weight in the composition.

As mentioned above, the oral composition of this invention is incorporated with a carboxylate compound, preferably a hydroxy-carboxylate compound. Using a carboxylate compound which does not contain a oxalic group in combination with oxalic acid compound produces the same effect as is produced when a phosphoric acid compound is incorporated. Thus preferred results are obtained when a carboxylate compound, particularly hydroxy-carboxylate compound is used in combination with an oxalic acid compound.

Preferred examples of the oxalic acid compound include oxalic acid and sodium salt, potassium salt, and ammonium salt thereof. They may be used alone or in combination with one another. The amount of oxalic acid compound is such that the solubilized portion thereof accounts for 0.07 to 5% by weight, preferably 0.1 to 3% by weight in the composition.

The oral composition of this invention may be incorporated with other ingredients according to the type and intended use of the composition.

Where the oral composition is used as dentifrices, it may be incorporated with an abrasive including calcium secondary phosphate (dihydrate or anhydrous), calcium primary phosphate, calcium tertiary phosphate, calcium carbonate, calcium pyrophosphate, titanium oxide, alumina, aluminum hydroxide, precipitated silica, other silica-based abrasive, aluminum silicate, insoluble sodium metaphosphate, insoluble potassium metaphosphate, magnesium tertiary phosphate, magnesium carbonate, calcium sulfate, bentonite, zirconium silicate, synthetic resin, etc., individually or in combination with one another. The amount to be added is usually 3 to 99% by weight; and 5 to 50% by weight in the case of toothpaste. The type and amount of the abrasive may preferably be selected so that the RAD value is 10 to 100, particularly 30 to 60.

Preferable among the above-mentioned abrasives is aluminum hydroxide. It permits the soluble aluminum compound to be stably incorporated in the composition. Aluminum hydroxide which is commercially available is satisfactory; but modified aluminum hydroxide which is obtained by treating aluminum hydroxide with an acid or a salt thereof disclosed in the Japanese patent application laid-open No. 59-122416 is preferable. It causes less astringent taste than ordinary aluminum hydroxide, and therefore the composition containing it gives a good feeling in use. Moreover, it is low in abrasiveness and consequently suitable where the oral composition is used for prevention or remedy of dentinal hypersensitivity.

Where the oral composition of this invention is used in the form of paste such as toothpaste, it is incorporated with one or more than one kind of binders such as carrageenan, cellulose derivatives (e.g., sodium carboxymethylcellulose, methylcellulose, hydroxyalkylcelluloses and sodium carboxymethyl-hydroxyethylcellulose), alkali metal alginates (e.g., sodium alginate), alginic acid-propylene glycol ester, gums (e.g., xanthane gum, tragacanth gum, calaya gum, and gum arabic), synthetic binders (e.g., polyvinyl alcohol, sodium polyacrylate, carboxy vinyl polymer, and polyvinyl pyrrolidone), and inorganic binders (e.g., gelling silica, gelling aluminum silicate, Veegum (trade name), and Laponite (trade name)). The binder is added in an amount of 0.1 to 10% by weight, and preferably 0.2 to 5% by weight.

Among the above-mentioned binders, a hydroxyalkylcellulose is preferable. Because of its good salt resistance, the hydroxyalkylcellulose permits the soluble aluminum compound to be stably incorporated in the oral composition and prevents the smoothness of the toothpaste from becoming rough.

Where the hydroxylalkylcellulose is used in combination with carrageenan, it improves the formability, syneresis, smoothness, stringing, and stability of the composition. Moreover, it eliminates the slimy feeling and improves the feeling in use, and permits the soluble aluminum compound to be incorporated in a stable manner with minimum deactivation of effective aluminum ions.

Where sodium carboxymethylcellulose, which is an anionic binder, is used, it reacts with aluminum ions to lower the concentration of effective aluminum ions in the composition, which in turn causes syneresis and smoothness of the composition. This is more pronounced when the composition is stored for a long period of time.

Where carrageenan, which is an anionic binder, is used, it adversely affects the stability (particularly syneresis and smoothness) of the composition, although it does not deactivate aluminum ions unlike sodium carboxylmethylcellulose.

Unexpectedly, the above-mentioned problems do not exist where hydroxyalkylcellulose and carrageenan are used in combination with each other. Using hydroxylalkylcellulose alone may aggravate the formability and stringing of the composition and make the composition feel slimy and taste unpleasant.

The preferred examples of the hydroxyalkylcellulose include hydroxyethylcellulose and hydroxypropylcellulose. In the case of the former, the amount of ethylene oxide added is 1.3 to 2.5 mol, preferably 1.8 to 2.2 mol; and in the case of the latter, the amount of propylene oxide added is 3.0 to 4.0 mol. They are effective in stabilizing more the composition. If the amount of ethylene oxide or propylene oxide added in the hydroxyalkylcellulose is less than the above-mentioned limits, the resulting composition may be poor in smoothness; and in the reverse case, the resulting composition may be poor in formability and stringing. Preferred the hydroxyalkylcellulose is one which has a solution viscosity of 2 to 6000 cps (1% in water).

Preferred carrageenan is $\lambda$-carrageenan which improves the smoothness of the composition. It may contain a certain amount of $\iota$- and $\kappa$-carrageenan so long as they do not adversely affect the properties of $\lambda$-carrageenan. The maximum permissible amount of $\iota$- and $\kappa$-carrageenan is about 50% in the total carrageenan.

The hydroxyalkylcellulose and carrageenan may be used in a ratio of 10:1 to 1:10, preferably be 3:1 to 1:5 by weight, and their total amount may be 0.1 to 10% by weight, particularly 0.5 to 5% by weight in the composition. If the hydroxyalkylcellulose is used in excess of the above-mentioned ratio or the total amount exceeds the above-mentioned limits, the resulting composition may be poor in stringing and feeling in use. If carrageenan is used in excess of the above-mentioned ratio or the total amount exceeds the above-mentioned limits, the resulting composition may be poor in syneresis and smoothness.

Where the composition is made in the form of toothpaste, liquid, or paste, it can be incorporated with one or more than one kind of humectants such as sorbitol, glycerin, ethylene glycol, propylene glycol, 1,3-butylene glycol, polyethylene glycol, polypropylene glycol, xylitol, multit, and lactit. The amount is usually 10 to 70% by weight.

Where the hydroxyalkylcellulose is used as a binder, it is preferable to use polyethylene glycol as a dispersing agent in order to prevent the smoothness of toothpaste from becoming rough. The roughening of the smoothness may occur where the hydroxylalkylcellulose is added together with propylene glycol or glycerin as a dispersing agent, because the viscosity of the dispersing agent increases to form an undissolved lump of the hydroxyalkylcellulose. This can be prevented if the hydroxyalkylcellulose is added together with polyethylene glycol, particularly one which is liquid at room temperature and has an average molecular weight of 300 to 400. Thus the hydroxylalkylcellulose is allowed to exhibit its performance as a binder, and consequently it is possible to incorporate a soluble aluminum compound and other salts without deteriorating the storage stability of the oral composition Preferred polyethylene glycol is one which is liquid at room temperature and has an average molecular weight of 300 to 400, as mentioned above. This polyethylene glycol thoroughly disperses the hydroxyalkylcellulose, preventing the smoothness from becoming rough. The amount of polyethylene glycol to be incorporated is 1 to 20% by weight, preferably 3 to 10% by weight. If the amount is less than 1% by weight, dispersion may be poor; and if it exceeds 20% by weight, the taste of the composition may be poor. The hydroxyalkylcellulose and polyethylene glycol may be used in a weight ratio of 1:2 to 1:30, particularly 1:5 to 1:20, for good dispersion. The hydroxylalkylcellulose is preferably dispersed in polyethylene glycol prior to incorporation into the oral composition.

The oral composition of this invention may be incorporated with one or more than one kind of anionic, nonionic, and amphoteric surface active agents. Examples of anionic surface active agents include water-soluble salts of higher alkyl ($C_8$–$C_{18}$) sulfate esters (e.g., sodium lauryl sulfate and sodium myristyl sulfate), water-soluble salts of higher fatty acid monoglyceride monosulfates (e.g., hydrogenated coconut fatty acid monoglyceride monosodium sulfate), water-soluble salts of alkylaryl sulfonates (e.g., sodium dodecylbenzenesulfonate), higher alkyl sulfonates, higher fatty acid esters (e.g., 1,2-dihydroxypropanesulfonate), and substantially saturated higher aliphatic acylamides of lower aliphatic aminocarboxylic acid compounds (e.g., sodium, potassium or ethanolamine salt of N-lauryol, N-myristoyl, or N-palmitoylsarcosine). Examples of nonionic surface active agents include fatty acid alkanolamides, sucrose fatty acid esters having a $C_{12}$–$C_{18}$ fatty acid group (e.g., sucrose monolaurate and sucrose dilaurate), lactose fatty acid esters, lactitol fatty acid esters, maltitol fatty acid esters, stearyl monoglyceride, and condensation products of polyethylene oxide with fatty acids, fatty alcohols, polyhydric alcohols, or polypropylene oxide (e.g., polyoxyethylene sorbitan monolaurate, polyoxyethylene sorbitan monosterate, polyoxyethylene (10, 20, 40, 60, 80, or 100 mol) hardened castor oil, polymers of ethylene oxide and propylene oxide, and polyoxyethylene-polyoxypropylene monolauryl ester). Examples of amphoteric surface active agents include betaine-derived or amino acid-derived ones. The amount of surface active agent is 0 to 7%, preferably 0.2 to 5%.

Among these surface active agents, a fatty acid alkanolamide is preferable. It reduces the astringent taste caused by an aluminum compound in the toothpaste. The astringent taste is attributable to aluminum ions that act on protein in the mouth. In addition, aluminum hydroxide used as an abrasive also has an astringent taste. Therefore, the astringent taste is amplified where a soluble aluminum compound and aluminum hydroxide are used together. The reactivity of a soluble aluminum compound in the mouth is reduced by a fatty acid alkanolamide. Thus the incorporation of the fatty acid alkanolamide reduces the astringent taste of the soluble aluminum compound and permits aluminum hydroxide as an abrasive to be added without undesirable side effect.

The preferred fatty acid alkanolamide is one having a $C_{10}$–$C_{16}$ (preferably $C_{12}$–$C_{14}$) fatty acid group and a $C_2$–$C_3$ alkanol group. The fatty acid may be a saturated one or unsaturated one, or straight-chain one or branched chain one. In addition, it may be a mixture of fatty acids. The preferred examples include caproyl monoethanolamide, lauroyl diethanolamide, myristoyl diethanolamide, palmitoyl diethanolamide, coconut oil fatty acid diethanolamide, beef tallow fatty acid diethanolamide, and lauryol monoisopropanolamide. Lauryol diethanolamide and myristoyl diethanolamide are particularly preferable.

The amount of the fatty acid alkanolamide is 0.1 to 5% by weight, preferably 0.3 to 3% by weight. If the amount is less than 0.1%, the astringent taste of the composition may not be sufficiently reduced.

The oral composition of this invention may be incorporated further with a sweetener such as sodium saccharin, stevioside, neohesperidyldihydrochalocone, glycyrrhizin, perillartine, thawmatin, asparatyl-pheylalanine methyl ester, p-methoxycinnamic aldehyde, lactose, fructose, and sodium cyclamate (0 to 1% by weight, preferably 0.01 to 0.5% by weight); a preservative such as p-hydroxymethylbenzoic acid, p-hydroxyethylbenzoic acid, p-hydroxybutyl benzoic acid, sodium benzoate, and lower fatty acid monoglyceride; and other ingredients such as gelatin, peptone, arginine hydrochloride, alubumin, casein, silicone, and coloring matter.

The oral composition should preferably be incorporated with l-menthol as a flavor. It reduces the metallic taste and astringent taste of a soluble aluminum compound. A soluble aluminum compound incorporated into the oral composition gives a marked astringent taste and metallic taste, or unpleasant feeling to the user. This feeling is associated with the pH of the composition that contains a soluble aluminum compound. The composition of pH 4 gives an astringent taste; but the astringent taste decreases at pH 5 or above, particularly at pH 6 or above. The composition still has a metallic taste. It was found that the astringent taste and metallic taste can be completely eliminated when the composition is incorporated with l-menthol at pH 5 or above. This effect is not produced by other flavors such as carvone, anethole, methyl salicylate, etc. Thus the oral composition containing a soluble aluminum compound can be greatly improved in taste when it is adjusted to pH 5 or above and incorporated with l-menthanol.

The l-menthol may be added in the form of essential oil such as peppermint oil that contains l-menthol. The amount of l-menthol is 0.01 to 10% by weight, preferably 0.1 to 6% by weight. If the amount is less than 0.01% by weight, the taste may not be improved satisfactorily, and if the amount exceeds 10% by weight, the composition may have an excessive cooling taste.

The oral composition of this invention may be incorporated, in addition to l-menthol, other flavors such as carvone, anethole, eugenol, methyl salicylate, spearmint oil, wintergreen oil, sassafras oil, clove oil, eucalyptus oil, etc. It is preferable to add, in addition to l-menthol, spice essential oil or spice oleoresin in an amount of 0.0001 to 1% by weight, particularly 0.001 to 3% by weight in the composition. They impart a delicate flavor and taste to the composition.

The oral composition in the form of toothpaste can be prepared by mixing the desired ingredients with a proper amount of water.

Where the oral composition of this invention is used in the form other than toothpaste, it can be produced in the usual manner from adequate ingredients.

The oral composition of this invention may be further incorporate with one or more than one kind of ϵ-aminocaproic acid, tranexamic acid, enzymes (such as dextranase, amylase, protease, mutanase, lysozyme, and lytic enzyme), alkali metal monofluorophosphates (such as sodium monofluorophosphate and potassium monofluorophosphate), fluorides (such as sodium fluoride, ammonium fluoride, and stannous fluoride), chlorhexidine hydrochloride, dihydrocholesterol, glycyrrhetic acid, chlorophyll, caropeptide, vitamins, anti-calculus agents, antibacterial agents, anti-plaque agents, and known dentinal desensitizers (such as potassium nitrate).

The oral composition of this invention may be produced from those which are properly selected from the above-mentioned ingredients. The composition should be adjusted to pH 5 or above, preferably pH 5 to pH 10, most preferably pH 6 to pH 8. The composition of low pH is not effective in preventing and remedying dentinal hypersensitivity. The pH adjustment can be accomplished by adding sodium hydroxide, sodium hydrogen carbonate, sodium carbonate, or the like.

The oral composition of this invention comprises containing therein aluminum and a carboxylate compound in solubilized state, with the molar ratio of a carboxylate compound to aluminum being lower than 6, and having a pH value higher than 5. It is effective for occlusion of tubular orifices and effectively prevents and remedies dentinal hypersensitivity.

The invention is now described with reference to the following examples, which are not intended to limit the scope of this invention.

EXAMPLE 1

A variety of chemical compounds were examined for occlusion of tubular orifices by using a split chamber device for measuring dentinal permeability, which directly measures in vitro the movement of the dentinal fluid that stimulates the nerve, causing dentinal hypersensitivity.

To be more specific, a dentin disk obtained from a human tooth is mounted on the device, and Ringer's solution is forced to pass through the dentinal tubules under pressure and the amount of Ringer's solution which has passed in a unit time is measured. The occlusion of tubular orifices is judged from the reduction in flow rate of Ringer's solution that passes through the dentin disk. This reduction varies depending on the ability of a chemical component to deposit around the tubular orifice and reduce the flow rate.

The chemical compounds used in this example are shown in Tables 1 to 4, together with their concentrations in water and pH adjusted with NaOH. The one side of dentin disk was dipped in each solution.

Tables 1 to 4 show the effect of each chemical compound on occlusion of tubular orifices. The effect was judged from the reduction rate (%) calculated from the following equation.

$$\text{Reduction rate (\%)} = (A - B)/A \times 100$$

where
A: the amount ($\mu$l) of Ringer's solution that passes through the untreated dentin disk in 10 minutes.
B: the amount ($\mu$l) of Ringer's solution that passes through the treated dentin disk in 10 minutes.

TABLE 1

| Aluminum carboxylate or other compound | Al concentration (%) | Molar ratio of carboxylate compound to Al | pH | Reduction rate (%) |
|---|---|---|---|---|
| Zinc lactate | 1.0* | — | 6.0 | 2.0 |
| Magnesium lactate | 1.0* | — | 6.0 | 1.0 |
| Aluminum chlorohydro-allantoinate | 0.3 | — | 6.0 | 3.3 |
| Aluminum chlorohydro-allantoinate | 3.0 | — | 6.0 | 8.5 |
| Aluminum dihydroxy-allantoinate | 0.3 | — | 6.0 | 0 |
| Aluminum EDTA | 0.3 | — | 6.0 | 0 |
| AlCl$_3$ | 0.3 | — | 3.0 | 0 |
| Al$_2$(SO$_4$)$_3$ | 0.3 | — | 3.5 | 0 |
| Aluminum lactate | 0.5 | 3/1 | 3.5 | 0 |
| Aluminum lactate | 0.5 | 3/1 | 4.5 | 8 |
| Aluminum lactate | 0.5 | 3/1 | 7.0 | 20 |
| Aluminum lactate | 0.5 | 3/1 | 8.0 | 73 |
| Aluminum glycolate | 0.5 | 3/1 | 7.0 | 23 |
| Aluminum glycolate | 0.5 | 3/1 | 9.0 | 79 |
| Aluminum malate | 0.7 | 1.5/1 | 2.5 | 0 |
| Aluminum malate | 0.7 | 1.5/1 | 9.0 | 63 |

*Concentration of zinc lactate or magnesium lactate.

TABLE 2

| Aluminum carboxylate | Al concentration (%) | Molar ratio of carboxylate compound to Al | pH | Reduction rate (%) |
|---|---|---|---|---|
| Aluminum monocarboxylate | | | | |
| Al(OH)$_3$ + Lactic acid | 0.5 | 2/1 | 7.0 | 52 |
| Al(OH)$_3$ + Lactic acid | 0.5 | 1.5/1 | 7.0 | 96 |
| Al(OH)$_3$ + Lactic acid | 0.5 | 1/1 | 7.0 | 23 |
| Al(OH)$_3$ + Gluconic acid | 0.5 | 2/1 | 7.0 | 63 |
| Al(OH)$_3$ + Gluconic acid | 0.5 | 1.5/1 | 7.0 | 98 |
| Al(OH)$_3$ | 0.5 | 1/1 | 7.0 | 25 |
| Aluminum dicarboxylate | | | | |
| Al(OH)$_3$ + Malonic acid | 0.5 | 1/1 | 7.0 | 50 |
| Al(OH)$_3$ + Malonic acid | 0.5 | 0.5/1 | 7.0 | 33 |
| Al(OH)$_3$ + Malonic acid | 0.5 | 0.25/1 | 7.0 | 29 |
| Al(OH)$_3$ + Malic acid | 0.5 | 1/1 | 7.0 | 45 |
| Al(OH)$_3$ + Malic acid | 0.5 | 0.5/1 | 7.0 | 36 |
| Al(OH)$_3$ + Malic acid | 0.5 | 0.25/1 | 7.0 | 31 |
| Al(OH)$_3$ + Tartaric acid | 0.5 | 1/1 | 7.0 | 90 |
| Al(OH)$_3$ + Tartaric acid | 0.5 | 0.5/1 | 7.0 | 40 |
| Al(OH)$_3$ + Tartaric acid | 0.5 | 0.25/1 | 7.0 | 36 |
| Aluminum tricarboxylate | | | | |
| Al(OH)$_3$ + Citric acid | 0.5 | 0.5/1 | 7.0 | 27 |
| Al(OH)$_3$ + Citric acid | 0.5 | 0.33/1 | 7.0 | 56 |
| Al(OH)$_3$ + Citric acid | 0.5 | 0.15/1 | 7.0 | 32 |

Each aluminum carboxylate was prepared by adding carboxylic acid to freshly prepared aluminum hydroxide so that the carboxylate compound to aluminum molar ratio is established as desired.

TABLE 3

| Aluminum carboxylate | Al concentration (%) | Molar ratio of carboxylate compound to Al | Additive compound | Additive compound concentration (%) | pH | Reduction rate (%) |
|---|---|---|---|---|---|---|
| Aluminum lactate | 0.5 | 3/1 | — | — | 7.0 | 20 |
|  |  | 3/1 | NaF | 0.22 | 7.0 | 26 |
| Aluminum lactate | 0.5 | 3/1 | Sodium monofluorophosphate | 0.8 | 7.0 | 22 |
| Aluminum lactate | 0.5 | 3/1 | $Na_3SO_4$ | 3.0 | 7.0 | 21 |
| Aluminum lactate | 0.5 | 3/1 | $Na_2HPO_4$ | 1.0 | 7.0 | 95 |
| Aluminum lactate | 0.5 | 3/1 | $Na_4P_2O_7$ | 0.5 | 6.0 | 88 |
| Aluminum lactate | 0.5 | 3/1 | $(NH_4)_2HPO_4$ | 1.0 | 7.0 | 84 |
| Aluminum lactate | 0.5 | 3/1 | Sodium tripolyphosphate | 3.0 | 7.0 | 99 |
| Aluminum lactate | 0.5 | 3/1 | Sodium hexametaphosphate | 1.2 | 7.0 | 87 |
| Aluminum lactate | 0.5 | 3/1 | Sodium glycerophosphate | 4.0 | 7.0 | 61 |
| Aluminum lactate | 0.5 | 3/1 | Sodium oxalate | 0.8 | 7.0 | 83 |
| Aluminum lactate | 0.5 | 3/1 | Ammonium oxalate | 1.0 | 7.0 | 91 |
| Aluminum lactate + Lactic acid | 0.5 | 4/1 | $KH_2PO_4$ | 2.0 | 6.0 | 74 |
| Aluminum malate | 0.5 | 1.5/1 | Sodium phytate | 0.5 | 6.0 | 38 |
| Aluminum malate | 0.1 | 1.5/1 | Ammonium oxalate | 0.8 | 7.0 | 71 |
| Aluminum tartrate | 0.5 | 1.5/1 | Sodium tripolyphosphate | 3.0 | 7.0 | 85 |
| Aluminum tartrate | 0.5 | 1.5/1 | Sodium hexametaphosphate | 2.0 | 5.0 | 68 |
| Aluminum citrate | 0.5 | 1/1 | Potassium oxalate | 4.0 | 7.0 | 70 |
| Aluminum citrate | 1.0 | 1/1 | Potassium oxalate | 5.0 | 8.0 | 79 |
| Aluminum citrate | 1.0 | 1/1 | Sodium phytate | 1.0 | 7.0 | 39 |
| Aluminum citrate | 0.5 | 1/1 | EHDP | 2.0 | 7.0 | 43 |

TABLE 4

| Aluminum carboxylate or other Al compound | Al concentration (%) | Molar ratio of carboxylate compound to Al | Additive compound | Additive compound concentration (%) | pH | Reduction rate (%) |
|---|---|---|---|---|---|---|
| $Al(OH)_3$ + Lactic acid | 0.5 | 1.5/1 | — | — | 5.3 | 85 |
| $Al(OH)_3$ + Lactic acid | 0.5 | 1.5/1 | $NaH_2PO_4$ | 0.2 | 6 | 96 |
| $Al(OH)_3$ + Lactic acid | 0.3 | 1.5/1 | Sodium oxalate | 0.2 | 6 | 92 |
| $Al(OH)_3$ + Gluconic acid | 0.5 | 2/1 | — | — | 7 | 63 |
| $Al(OH)_3$ + Gluconic acid | 0.5 | 2/1 | $Na_4P_2O_7$ | 0.2 | 7 | 92 |
| $Al(OH)_3$ + Tartaric acid | 0.2 | 1/1 | — | — | 7 | 50 |
| $Al(OH)_3$ + Tartaric acid | 0.2 | 1/1 | Sodium tripolyphosphate | 1.0 | 7 | 78 |
| $Al(OH)_3$ + Malonic acid | 0.5 | 1/1 | — | — | 7 | 40 |

TABLE 4-continued

| Aluminum carboxylate or other Al compound | Al concentration (%) | Molar ratio of carboxylate compound to Al | Additive compound | Additive compound concentration (%) | pH | Reduction rate (%) |
|---|---|---|---|---|---|---|
| Al(OH)$_3$ + Malonic acid | 0.5 | 1/1 | Na$_4$P$_2$O$_7$ | 0.2 | 7 | 65 |
| Al(OH)$_3$ + Citric acid | 0.5 | 0.5/1 | — | — | 7 | 27 |
| Al(OH)$_3$ + Citric acid | 0.5 | 0.5/1 | NaH$_2$PO$_4$ | 0.4 | 6 | 53 |
| Al(OH)$_3$ + Citric acid | 0.5 | 0.3/1 | — | — | 6 | 30 |
| Al(OH)$_3$ + Citric acid | 0.5 | 0.3/1 | Sodium oxalate | 0.3 | 6 | 72 |

Tables 1 to 4 indicate that aluminum carboxylate at pH 5 or up is effective for occlusion of tubular orifices, and that the effect of aluminum carboxylate is improved when a phosphoric acid compound or oxalic acid compound is used together.

EXAMPLE 2

A toothpaste was prepared according to the formulation given in Table 5. The toothpaste was filled in a tube and stored in a thermostat at 50° C. for 1 month. The toothpaste was examined for retention of soluble aluminum compound (aluminum lactate), formability, syneresis, smoothness, stringing, and feeling in use. The criteria for the organoleptic tests are as follows: The results are shown in Table 5.

Formability (observed when extruded from the tube):
  o: Placing the toothpaste on a toothbrush is easy due to proper stiffness.
  Δ: Placing the toothpaste on a toothbrush is a little difficult.
  x: Placing the toothpaste on a toothbrush is difficult.
Syneresis (observed when extruded from the tube):
  o: There is no ooze of liquid.
  Δ: There is a little ooze of liquid.
  x: There is much ooze of liquid.
Smoothness (observed when extruded from the tube):
  o: Smooth texture.
  Δ: Slightly rough texture.
  x: Severely rough texture.
Stringing (observed when extruded from the tube):
  o: Not ropy.
  Δ: Slightly ropy.
  x: Severely ropy.
Retention of soluble aluminum compound (determined according to the procedure given below):
  o: 80 to 100%
  Δ: 60 to 80%
  x: less than 60%
Feeling in use (stickiness feeling when used in the normal manner):
  o: Not stickiness
  Δ: Slightly stickiness
  x: Severely stickiness
Determination of residual soluble aluminum compound:

5.0 g of a toothpaste sample was dispersed in 100 ml of purified water, and the dispersion was centrifuged at 10,000 rpm for 10 minutes. 10 g of the supernatant liquid was taken and the amount of residual aluminum compound was determined by EDTA titration.

$$\text{Retention (\%)} = A/B \times 100$$

where
  A: Amount determined after storage at 50° C. for 1 month.
  B: Amount determined immediately after preparation.

It is noted from Table 5 that where hydroxyethylcellulose and carrageenan are used together as a binder, the resulting toothpaste is good in storage stability and gives a good feeling in use and permits a soluble aluminum compound to remain stable. It is also noted that aluminum hydroxide as an abrasive improves the stability of toothpaste and stabilizes the soluble aluminum compound.

TABLE 5

| Ingredient | 1 | 2 | 3 | 4 | 5 | 6 | 7 | 8 | 9 | 10 | 11 | 12 | 13 |
|---|---|---|---|---|---|---|---|---|---|---|---|---|---|
| Calcium secondary phosphate | | | | | | | | | | 45% | | | |
| Calcium carbonate | | | | | | | | | | | 45% | | |
| Silica | | | | | | | | | | | | 30% | |
| Aluminum hydroxide | 45% | 45% | 45% | 45% | 45% | 45% | 45% | 45% | 45% | | | | 45% |
| Sodium carboxymethylcellulose | 1.0 | | | | | | | | | | | | |
| Carrageenan | | 1.0 | | | | | 0.3 | 0.5 | 0.8 | 0.5 | 0.5 | 0.5 | 0.5 |
| Hydroxyethylcellulose | | | 1.0 | | | | 0.7 | 0.5 | 0.2 | 0.5 | 0.5 | 0.5 | 0.5 |
| Sodium alginate | | | | 1.0 | | | | | | | | | |
| Xanthane gum | | | | | 1.0 | | | | | | | | |

TABLE 5-continued

| Ingredient | 1 | 2 | 3 | 4 | 5 | 6 | 7 | 8 | 9 | 10 | 11 | 12 | 13 |
|---|---|---|---|---|---|---|---|---|---|---|---|---|---|
| Sodium polyacrylate | | | | | | 1.0 | | | | | | | |
| Polyethylene glycol | 5.0 | 5.0 | 5.0 | 5.0 | 5.0 | 5.0 | 5.0 | 5.0 | 5.0 | 5.0 | 5.0 | 5.0 | 5.0 |
| Sorbitol | 30 | 30 | 30 | 30 | 30 | 30 | 30 | 30 | 30 | 30 | 30 | 30 | 30 |
| Aluminum lactate | 3.0 | 3.0 | 3.0 | 3.0 | 3.0 | 3.0 | 3.0 | 3.0 | 3.0 | 3.0 | 3.0 | 3.0 | 3.0 |
| Sodium lauryl sulfate | 0.5 | 0.5 | 0.5 | 0.5 | 0.5 | 0.5 | 0.5 | 0.5 | 0.5 | 0.5 | 0.5 | 0.5 | 0.5 |
| Sodium saccharin | 0.1 | 0.1 | 0.1 | 0.1 | 0.1 | 0.1 | 0.1 | 0.1 | 0.1 | 0.1 | 0.1 | 0.1 | 0.1 |
| Flavor | 1.0 | 1.0 | 1.0 | 1.0 | 1.0 | 1.0 | 1.0 | 1.0 | 1.0 | 1.0 | 1.0 | 1.0 | 1.0 |
| Sodium hydroxide | Trace | Trace | Trace | Trace | Trace | Trace | Trace | Trace | Trace | Trace | Trace | Trace | Trace |
| Purified water | Balance | Balance | Balance | Balance | Balance | Balance | Balance | Balance | Balance | Balance | Balance | Balance | Balance |
| Total (%) | 100.0% | 100.0% | 100.0% | 100.0% | 100.0% | 100.0% | 100.0% | 100.0% | 100.0% | 100.0% | 100.0% | 100.0% | 100.0% |
| Toothpaste pH | 7 | 7 | 7 | 7 | 7 | 7 | 7 | 7 | 7 | 6.5 | 8 | 6 | 7 |
| Items for evaluation | | | | | | | | | | | | | |
| Formability | o | o | Δ~x | Δ | Δ | o | o | o | o | o | o | o | o |
| Syneresis | x | Δ | o | x | o | x | o | o | o | Δ | Δ | x | o |
| Smoothness | x | x | o | x | x | x | o | o | o | x | x | Δ | o |
| Stringing | Δ | o | x | Δ | x | Δ | o~Δ | o | o | o | o | o | o |
| Retention of Al$^{3+}$ | x | o | o | Δ | Δ | Δ | o | o | o | x | x | x | o |
| Feeling in use (stickiness) | o | o | x | Δ | x | Δ | o | o | o | o | o | o | o |

EXAMPLE 3

A toothpaste was prepared according to the formulation given below. The toothpaste was visually examined for smoothness according to the criterion which is given after the formulation. The results are shown in Table 6.

| Formulation of toothpaste: | |
|---|---|
| Aluminum hydroxide | 45% |
| Hydroxyethylcellulose (M.S. 2.0, 1% visc. 1500 cp) | 0.7 |
| Carrageenan | 0.3 |
| Sorbitol | 30 |
| Aluminum lactate | 5.0 |
| Sodium lauryl sulfate | 1.0 |
| Flavor | 1.0 |
| Dispersing agent | 5.0 |
| NaOH | Trace |
| Purified water | Balance |
| Total | 100.0 |

Hydroxyethylcellulose was added to the dispersing agent, followed by thorough mixing. The toothpaste had pH 7.
Criterion for evaluating the smoothness:
  o: Smooth and glossy texture.
  Δ: Slightly rough texture.
  x: Severely rough texture.

It is noted from Table 6 that when polyethyleneglycol with an average molecular weight of 200 to 400, particularly 300 to 400 is used as a dispersing agent, the resulting toothpaste has good smoothness.

TABLE 6

| Dispersing agent | Smoothness |
|---|---|
| Polyethylene glycol 200 | o - Δ |
| Polyethylene glycol 300 | o |
| Polyethylene glycol 400 | o |
| Polyethylene glycol 600 | Δ- x |
| Propylene glycol | x |
| Glycerin | x |

EXAMPLE 4

Seven kinds of toothpaste were prepared according to the formulation given in Table 7. They were examined for astringent taste and metallic taste in the organoleptic manner by 10 expert panelists according to the following criterion. The results are shown Table 7.
Criterion for evaluation:
  o: No astringent taste:
  Δ: Slight astringent taste.
  x: Strong astringent taste.

It is noted from Table 7 that the taste of the toothpaste can be improved when the composition containing a soluble aluminum compound (aluminum lactate) and aluminum hydroxide is incorporated with a fatty acid alkanolamide, particularly lauroyl and myristoyl diethanolamide. As an abrasive, modified aluminum hydroxide is more preferable than aluminum hydroxide.

TABLE 7

| Ingredient | 14 | 15 | 16 | 17 | 18 | 19 | 20 |
|---|---|---|---|---|---|---|---|
| Aluminum hydroxide | 40% | 40% | 40% | 40% | 40% | 40% | |
| Modified aluminum hydroxide | | | | | | | 40% |
| Sorbitol | 30 | 30 | 30 | 30 | 30 | 30 | 30 |
| Polyethylene glycol 400 | 5 | 5 | 5 | 5 | 5 | 5 | 5 |
| Carrageenan | 0.7 | 0.7 | 0.7 | 0.7 | 0.7 | 0.7 | 0.7 |
| Hydroxyethylcellulose | 0.3 | 0.3 | 0.3 | 0.3 | 0.3 | 0.3 | 0.3 |
| Saccharin | 0.1 | 0.1 | 0.1 | 0.1 | 0.1 | 0.1 | 0.1 |
| Caproyl diethanolamide | | 0.5 | | | | | |

TABLE 7-continued

| Ingredient | 14 | 15 | 16 | 17 | 18 | 19 | 20 |
|---|---|---|---|---|---|---|---|
| Lauroyl diethanolamide | | | 0.5 | | | | |
| Myristoyl diethanolamide | | | | 0.5 | | 0.3 | 0.3 |
| Palmitoyl diethanolamide | | | | | 0.5 | | |
| Sodium lauryl sulfate | 0.5 | 0.5 | 0.5 | 0.5 | 0.5 | 0.5 | 0.5 |
| Carvone | 0.1 | 0.1 | 0.1 | 0.1 | 0.1 | 0.1 | 0.1 |
| Anethole | 0.3 | 0.3 | 0.3 | 0.3 | 0.3 | 0.3 | 0.3 |
| Orange oil | 0.05 | 0.05 | 0.05 | 0.05 | 0.05 | 0.05 | 0.05 |
| Aluminum lactate | 3 | 3 | 3 | 3 | 3 | 3 | 3 |
| Sodium hydroxide | Trace | Trace | Trace | Trace | Trace | Trace | Trace |
| Purified water | Balance | Balance | Balance | Balance | Balance | Balance | Balance |
| Total | 100.0 | 100.0 | 100.0 | 100.0 | 100.0 | 100.0 | 100.0 |
| Toothpaste pH | 5 | 5 | 5 | 5 | 5 | 5 | 5 |
| Astringent taste | x | o∼Δ | o | o | o∼Δ | o∼Δ | o |

EXAMPLE 5

Seven kinds of toothpaste were prepared according to the formulation given in Table 8. They were examined for astringent taste and metallic taste in the organoleptic manner by 10 expert panelists according to the following criterion. The results are shown in Table 8.

Criterion for evaluation:
o: No astringent taste.
Δ: Slight astringent taste.
x: Strong astringent taste.

It is noted from Table 8 that the taste of the toothpaste can be improved when the composition contains l-menthol and has pH 5 or up. This improvement is not made by other flavor than l-menthol. In other words, it is only l-menthol that improves the taste of the oral composition containing a soluble aluminum compound. Even in the case where l-menthol is added, the improvement by it is made if the composition has pH 5 or below. Thus, if the composition containing a soluble aluminum compound is to be improved in its taste, it is necessary to add l-menthol and keep the composition at pH 5.

EXAMPLE 6

| Toothpaste: | |
|---|---|
| Polyethylene glycol #400 | 3% |
| Hydroxyethylcellulose | 2 |
| Sorbitol | 30 |
| Modified aluminum hydroxide | 40 |
| Sodium lauryl sulfate | 0.3 |
| l-menthol | 0.5 |
| Sodium saccharin | 0.1 |
| Aluminum lactate | 5.0 |
| Purified water | Balance |
| Total | 100.0% | pH = 7.0 (adjusted with sodium hydroxide)

EXAMPLE 7

| Toothpaste: | |
|---|---|
| Propylene glycol | 5% |
| Carrageenan | 2 |
| Gelatin | 0.3 |
| Sorbitol | 15 |

TABLE 8

| Ingredient | 21 | 22 | 23 | 24 | 25 | 26 | 27 |
|---|---|---|---|---|---|---|---|
| Aluminum hydroxide | 50% | 50% | 50% | 50% | 50% | 50% | 50% |
| Polyethylene glycol 400 | 5 | 5 | 5 | 5 | 5 | 5 | 5 |
| Hydroxyethylcellulose | 0.5 | 0.5 | 0.5 | 0.5 | 0.5 | 0.5 | 0.5 |
| Carrageenan | 0.5 | 0.5 | 0.5 | 0.5 | 0.5 | 0.5 | 0.5 |
| Sorbitol | 20 | 20 | 20 | 20 | 20 | 20 | 20 |
| Sodium lauryl sulfate | 1 | 1 | 1 | 1 | 1 | 1 | 1 |
| Aluminum lactate | 2 | 2 | 2 | 2 | 2 | 2 | 2 |
| Sodium saccharin | 0.1 | 0.1 | 0.1 | 0.1 | 0.1 | 0.1 | 0.1 |
| Ethylparaben | 0.05 | 0.05 | 0.05 | 0.05 | 0.05 | 0.05 | 0.05 |
| Butylparaben | 0.05 | 0.05 | 0.05 | 0.05 | 0.05 | 0.05 | 0.05 |
| l-menthol | 0.5 | | 0.5 | | | | 0.5 |
| l-carvone | | 0.5 | | 0.5 | | | |
| Anethole | | | | | 0.5 | | |
| Methyl salicylate | | | | | | 0.5 | |
| Sodium hydroxide | Trace | Trace | Trace | Trace | Trace | Trace | Trace |
| Purified water | Balance | Balance | Balance | Balance | Balance | Balance | Balance |
| Total | 100.0% | 100.0% | 100.0% | 100.0% | 100.0% | 100.0% | 100.0% |
| Composition pH | 3.5 | 3.5 | 6.5 | 6.5 | 6.5 | 6.5 | 8 |
| Astringent taste | x | x | o | o∼Δ | Δ | o∼Δ | o |
| Metallic taste | x | x | o | x∼Δ | x∼Δ | x | o |

-continued

| Toothpaste: | |
|---|---|
| Aluminum hydroxide | 40 |
| Sodium lauryl sulfate | 0.5 |
| Flavor | 0.5 |
| Sodium saccharin | 0.05 |
| Aluminum lactate | 1.0 |
| Potassium nitrate | 5.0 |
| Disodium phosphate | 0.6 |
| Sodium monofluorophosphate | 0.76 |
| Purified water | Balance |
| Total | 100.0% | pH=6.0 (adjusted with sodium hydroxide)

EXAMPLE 8

| Toothpaste: | |
|---|---|
| Propylene glycol | 3% |
| Carrageenan | 1.5 |
| Sorbitol | 35 |
| Glycerin | 20 |
| Modified aluminum hydroxide | 20 |
| Sodium benzoate | 0.5 |
| Sodium lauryl sulfate | 1.5 |
| Flavor | 1.0 |
| Sodium saccharin | 0.03 |
| Aluminum lactate | 7.0 |
| Purified water | Balance |
| Total | 100.0% | pH=8.5 (adjusted with sodium hydroxide)

EXAMPLE 9

| Toothpaste: | |
|---|---|
| Propylene glycol | 3% |
| Xanthane gum | 2 |
| Glycerin | 20 |
| Alumina | 10 |
| Sodium lauryl sulfate | 2.0 |
| Flavor | 0.3 |
| Sodium saccharin | 0.05 |
| Aluminum citrate | 3.5 |
| Sodium pyrophosphate | 1.0 |
| Chlorohexidine gluconate | 0.05 |
| Purified water | Balance |
| Total | 100.0% | pH=5.5 (adjusted with sodium hydroxide)

EXAMPLE 10

| Toothpaste: | |
|---|---|
| Polyethylene glycol #300 | 5% |
| Hydroxyethylcellulose | 2.5 |
| Sodium carboxymethylcellulose | 0.5 |
| Ethylparaben | 0.05 |
| Sorbitol | 30 |
| Glycerin | 10 |
| Calcium pyrophosphate | 20 |
| Sodium lauryl sulfate | 1.0 |
| Sodium lauroyl sacrosinate | 0.5 |
| Lauroyl diethanolamide | 0.5 |
| Flavor | 1.0 |
| Sodium saccharin | 0.2 |
| Aluminum lactate | 3.0 |
| Aluminum tartrate | 6.0 |
| Potassium nitrate | 4.0 |
| Sodium fluoride | 0.22 |
| Purified water | Balance |
| Total | 100.0% | pH=6.5 (adjusted with sodium hydroxide)

EXAMPLE 11

| Toothpaste: | |
|---|---|
| Polyethylene glycol #400 | 3% |
| Hydroxyethylcellulose | 1 |
| Carrageenan | 2 |
| Sorbitol | 20 |
| Insoluble sodium metaphosphate | 10 |
| Sucrose monolaurate | 2.0 |
| l-menthol | 0.8 |
| Peppermint oil | 0.4 |
| Anethole | 0.1 |
| Sodium saccharin | 0.1 |
| Aluminum malate | 4.0 |
| Sodium monofluorophosphate | 0.76 |
| Purified water | Balance |
| Total | 100.0% | pH=8 (adjusted with sodium hydroxide)

EXAMPLE 12

| Toothpaste: | |
|---|---|
| Polyethylene glycol #400 | 3% |
| Hydroxyethylcellulose | 1.5 |
| Carrageenan | 1.5 |
| Gelatin | 0.5 |
| Sorbitol | 50 |
| Modified aluminum hydroxide | 25 |
| Sodium lauryl sulfate | 0.5 |
| Sucrose laurate | 1.0 |
| Buthyl paraben | 0.01 |
| Ethyl paraben | 0.05 |
| Star anise oil | 0.05 |
| l-menthol | 0.7 |
| Orange oil | 0.1 |
| Clove oil | 0.08 |
| Eucalyptus oil | 0.07 |
| Aluminum lactate | 10 |
| Disodium phosphate | 2 |
| Sodium fluoride | 0.5 |
| Purified water | Balance |
| Total | 100.0% | pH=7 (adjusted with sodium hydroxide)

EXAMPLE 13

| Mouthwash: | |
|---|---|
| Glycerin | 5.0% |
| Sorbitol | 5.0 |
| Ethanol | 10 |
| Sodium saccharin | 0.15 |
| Sodium lauryl sulfate | 3.0 |
| l-menthol | 0.6 |
| Peppermint oil | 0.4 |
| Pimento oil | 0.05 |
| Coloring matter | 0.01 |
| Aluminum lactate | 2.0 |
| Disodium phosphate | 0.4 |
| Purified water | Balance |
| Total | 100.0% | pH=7.0 (adjusted with potassium hydroxide)

EXAMPLE 14

| Mouthwash: | |
|---|---|
| Glycerin | 10% |
| Sorbitol | 10 |
| Ethanol | 10 |

-continued

| Mouthwash: | |
|---|---|
| Sodium saccharin | 0.1 |
| Sodium lauryl sulfate | 1.0 |
| Flavor | 0.3 |
| Coloring matter | 0.01 |
| Aluminum lactate | 5.0 |
| $(NH_4)_2HPO_4$ | 1.0 |
| Sodium monofluorophosphate | 0.8 |
| Potassium nitrate | 5.0 |
| Purified water | Balance |
| Total | 100.0% | pH=7.0 (adjusted with postassium hydroxide)

EXAMPLE 15

| Mouthwash: | |
|---|---|
| Glycerin | 10% |
| Sorbitol | 10 |
| Ethanol | 10 |
| Sodium saccharin | 0.1 |
| Sodium lauryl sulfate | 2.0 |
| l-menthol | 0.5 |
| Coloring matter | 0.01 |
| Aluminum citrate prepared by adding 0.5 mols of citric acid to 1 mol of freshly prepared aluminum hydroxide | 2.0 |
| Disodium phosphate | 0.5 |
| Sodium oxalate | 1.0 |
| Sodium fluoride | 0.11 |
| Chlorhexidine gluconate | 0.01 |
| Purified water | Balance |
| Total | 100.0% | pH=6.5 (adjusted with potassium hydroxide)

EXAMPLE 16

| Mouthwash: | |
|---|---|
| Glycerin | 10% |
| Sorbitol | 10 |
| Ethanol | 10 |
| Sodium saccharin | 0.1 |
| Sodium lauryl sulfate | 1.0 |
| Buthyl paraben | 0.1 |
| Coloring matter | 0.01 |
| Aluminum lactate | 5.0 |
| Purified water | Balance |
| Total | 100.0% | pH=8.5 (adjusted with potassium hydroxide)

EXAMPLE 17

| Oral band: | |
|---|---|
| Sodium carboxymethylcellulose | 0.5% |
| Polyvinyl alcohol | 0.5 |
| Hydroxypropylcellulose | 9.0 |
| Polyethylene glycol 4000 | 1.0 |
| Flavor | 0.3 |
| Coloring matter | 0.05 |
| Aluminum lactate | 2.0 |
| Disodium phosphate | 0.4 |
| Purified water | Balance |
| Total | 100.0% | pH=7 (adjusted with sodium hydroxide)

EXAMPLE 18

| Oral band: | |
|---|---|
| Sodium carboxymethylcellulose | 0.5% |
| Polyvinyl alcohol | 0.5 |
| Hydroxypropylcellulose | 9.0 |
| Polyethylene glycol 4000 | 1.0 |
| l-menthol | 0.3 |
| Coloring matter | 0.05 |
| Aluminum lactate prepared by adding 1.5 mols of lactic acid to 1 mol of freshly prepared aluminum hydroxide | 3.0 |
| Sodium fluoride | 0.1 |
| Purified water | Balance |
| Total | 100.0% | pH=5.3 (not adjusted)

EXAMPLE 19

| Oral band: | |
|---|---|
| Sodium carboxymethylcellulose | 0.5% |
| Polyvinyl alcohol | 0.5 |
| Hydroxypropylcellulose | 9.0 |
| Polyethylene glycol 4000 | 1.0 |
| Buthyl paraben | 0.05 |
| Ethyl paraben | 0.03 |
| Sodium benzoate | 0.3 |
| l-menthol | 0.3 |
| Peppermint oil | 0.4 |
| l-carvone | 0.1 |
| Thyme oil | 0.08 |
| Sage oil | 0.06 |
| Pimento oleoresin | 0.04 |
| Amyl alcohol | 0.02 |
| Aluminum lactate | 10.0 |
| $KH_2PO_4$ | 2.0 |
| Sodium pyrophosphate | 2.0 |
| Purified water | Balance |
| Total | 100.0 | pH=7.5 (adjusted with sodium hydroxide)

The oral bands in Examples 17 to 19 were prepared by dissolving the specified ingredients in 100 g of water, freeze-drying the solution to remove water as far as possible, and forming the residues into film.

EXAMPLE 20

| Ointment: | |
|---|---|
| Hydroxypropylcellulose | 4.0% |
| Sorbitol | 40 |
| Flavor | 1.0 |
| Sodium saccharin | 0.03 |
| Buthyl paraben | 0.01 |
| Aluminum lactate | 5.0 |
| Disodium phosphate | 1.2 |
| Gelatin | 0.1 |
| Sodium lauryl sulfate | 0.1 |
| Purified water | Balance |
| Total | 100.0% | pH=7.0 (adjusted with sodium hydroxide)

EXAMPLE 21

| Ointment: | |
|---|---|
| Carrageenan | 4.5% |
| Propylene glycol | 5.0 |
| Glycerin | 10 |
| Sorbitol | 30 |

-continued

Ointment:

| | |
|---|---|
| l-menthol | 1.0 |
| Sodium saccharin | 0.03 |
| Ethyl paraben | 0.01 |
| Aluminum lactate prepared by the same procedure as Example 18 (Al: lactic acid = 1:1.5 (by mol)) | 5.0 |
| Sodium fluoride | 0.22 |
| Lauroyl diethanolamide | 0.2 |
| Sodium lauryl sulfate | 0.1 |
| Purified water | Balance |
| Total | 100.0% | pH=6.9 (adjusted with sodium hydroxide)

EXAMPLE 22

Ointment:

| | |
|---|---|
| Hydroxyethylcellulose | 2.0% |
| Sodium carboxymethylcellulose | 2.0 |
| Propylene glycol | 5.0 |
| Glycerin | 20 |
| Sorbitol | 20 |
| l-menthol | 0.6 |
| Sage oil | 0.05 |
| Pimento oil | 0.05 |
| l-carvone | 0.2 |
| Sodium saccharin | 0.03 |
| Methyl paraben | 0.01 |
| Aluminum lactate | 10 |
| $K_2HPO_4$ | 2.0 |
| Sodium monofluorophosphate | 1.6 |
| Potassium nitrate | 5.0 |
| Purified water | Balance |
| Total | 100.0% | pH=7.0 (adjusted with sodium hydroxide)

What is claimed is:

1. An oral composition for preventing and remedying dentinal hypersensitivity, comprising:
   an aluminum and a carboxylate compound in a solubilized state wherein the carboxylate compound is a monocarboxylate compound selected from the group consisting of lactate, gluconate and glycolate;
   the content of the solubilized aluminum is 0.01 to 10% by weight of the total weight of the composition;
   the molar ratio of the carboxylate compound to aluminum is 0.7 to 4; and
   the pH of the composition is higher than 5.
2. The composition as claimed in claim 1, wherein the molar ratio of the carboxylate compound to aluminum is 0.1 to 6.
3. The composition as claimed in claim 2, wherein the carboxylate compound is a monocarboxylate compound and the molar ratio of the monocarboxylate compound to aluminum is 0.7 to 4.
4. The composition as claimed in claim 2, wherein the carboxylate compound is a dicarboxylate compound and the molar ratio of the dicarboxylate compound to aluminum is 0.2 to 2.5.
5. The composition as claimed in claim 2, wherein the carboxylate compound is a tricarboxylate compound and the molar ratio of the tricarboxylate compound to aluminum is 0.1 to 2.
6. The composition as claimed in claim 1, wherein the pH value of the composition is 5 to 10.
7. The composition as claimed in claim 1, wherein the carboxylate compound is a compound having both carboxyl and hydroxyl groups.
8. The composition as claimed in claim 7, wherein the carboxylate compound is a monocarboxylate compound having at least one hydroxyl group.
9. The composition as claimed in claim 1, wherein the content of the solubilized aluminum is 0.01 to 10% by weight on the total weight of the composition.
10. An oral composition for preventing and remedying dentinal hypersensitivity, comprising:
    an effective amount of an aluminum and a carboxylate compound with the proviso that the carboxylate compound excludes oxylates in a solubilized state, wherein the molar ratio of the carboxylate compound to aluminum is lower than 6, the pH of the composition is higher than 5; and
    an effective amount of water-soluble phosphoric acid compound.
11. The composition as claimed in claim 10, wherein the phosphoric acid compound is at least one compound selected from the group consisting of orthophosphoric acid, glycerophosphoric acid, pyrophosphoric acid, tripolyphosphoric acid, hexametaphosphoric acid, phytic acid, and ethane-1-hydroxy-1,1-diphosphonic acid, and sodium salt, potassium salt, and ammonium salt thereof.
12. The composition as claimed in claim 10, wherein the content of the phosphoric acid compound is 0.01 to 10% by weight of the composition.
13. The composition as claimed in claim 1, wherein an oxalic acid compound is incorporated in combination with a carboxylate compound which does not contain an oxalic group.
14. The composition as claimed in claim 13, wherein the content of the oxalic acid compound is 0.07 to 5% by weight of the composition.
15. The composition as claimed in claim 1, wherein aluminum hydroxide is incorporated as a main abrasive.
16. The composition as claimed in claim 15, wherein aluminum hydroxide is acid treated aluminum hydroxide or salt treated aluminum hydroxide.
17. The composition as claimed in claim 1, wherein a hydroxyalkylcellulose is incorporated as a binder.
18. The composition as claimed in claim 1, wherein a hydroxyalkylcellulose and carrageenan are incorporated as a combined binder.
19. The composition as claimed in claim 17, wherein polyethylene glycol is incorporated as a dispersing agent of the hydroxyalkylcellulose.
20. The composition as claimed in claim 1, wherein a fatty acid alkanolamide is incorporated.
21. The composition as claimed in claim 20, wherein the fatty acid ester is lauroyl diethanolamide or myristoryl diethanolamide.
22. The composition as claimed in claim 1, wherein l-menthol is incorporated as a flavor.
23. A composition as claimed in claim 18, wherein polyethylene glycol is incorporated as dispersing agent of the hydroxyalkycellulose.
24. The composition as claimed in claim 10, wherein the alumium and carboxylate compound is an aluminum carboxylate selected from the group consisting of lactate, aluminum gluconate, aluminum glycolate, aluminum malonate, aluminum glutarate, aluminum malate, aluminum tartrate and aluminum citrate.
25. The composition as claimed in claim 1, wherein the aluminum compounds are selected from the group consisting of Al(NH$_4$)(SO$_4$)$_2$, AlCl$_3$, AlF$_3$, [Al(OH)$_2$Cl]$_x$, Al(NO$_3$)$_3$, KAL(SO$_4$)$_2$, Al$_2$(SO$_4$)$_3$ and Al(SiF$_6$)$_3$.

26. The composition as claimed in claim 10, wherein the carboxylate compound is a monocarboxylate compound having at least one hydroxyl group selected form the group consisting of lactic acid, glycolic acid, gluconic acid, and salts thereof.

27. The composition as claimed in claim 1, in the form of a dentifrice and further containing an abrasive selected form the group consisting of calcium secondary phosphate, calcium primary phosphate, calcium tertiary phosphate, calcium carbonate, calcium pyrophosphate, titanium oxide, alumina, aluminum hydroxide, precipitated silica, aluminum silicate, insoluble sodium metaphosphate, insoluble potassium metaphosphate, magnesium tertiary phosphate, magnesium carbonate, calcium sulfate, bentonite, zirconium silicate, synthetic resin, and mixtures thereof.

28. The composition as claimed in claim 27, wherein the amount of abrasive is 3 to 99% by weight.

29. The composition as claimed in claim 1, which is used in the form of paste and further comprises binders selected from the group consisting of carrageenan, sodium carboxymethylcellulose, methylcellulose, hydroxyalkylcelluloses, sodium carboxymethylhydroxyethylcellulose, sodium alginate, xanthane gum, tragacanth gum, calaya gum, gum arabic, polyvinvyl alcohol, sodium polyacrylate, carboxy vinyl polymer, polyvinvyl pyrrolidone, gelling silica and gelling alumium silicate.

30. The composition as claimed in claim 29, wherein the binder is present in an amount of 0.1 to 10% by weight.

31. The composition as claimed in claim 17, wherein the hydroxyalkylcellulose is selected from the group consisting of hydroxyethylcellulose containing 1.3 to 2.5 mol ethylene oxide and hydroxypropylcellulose containing 3.0 to 4.0 propylene oxide.

32. The composition as claimed in claim 17, wherein the hydroxyalkylcellulose has a solution viscosity of 2 to 6000 cps.

33. The composition as claimed in claim 18, wherein the hydroxylalkycellulose and carrageenan are in ratio of 10:1 to 1:10 by weight in the composition.

34. The composition as claimed in claim 19, wherein the polyethylene glycol has an average molecular weight of 300 to 400 and is present in an amount of 1 to 20% by weight.

35. The composition as claimed in claim 19, wherein the hydroxyalkylcellulose and polyethylene glycol are in a weight ratio of 1:2 to 1:30.

36. The composition as claimed in claim 20, wherein the fatty acid alkanolamide is present in an amout of 0.1 to 5% by weight and is selected from the group consisting of caproyl monoethanolamide, lauroyl diethanolamide, myristoyl diethanolamide, palmitoyl diethanolamide, coconut oil fatty acid diethanolamide, beef tallow fatty acid diethanolamide, and lauryol monoisopropanolamide.

37. The composition as claimed in claim 1, further comprising:
10 to 17% by weight of a humectant selected from the group consisting of sorbitol, glycerin, ethylene glycol, propylene glycol, 1,3-butylene glycol, polyethylene glycol, polypropylene glycol, xylitol, multit, and lactit; or 0 to 7% by weight of a surface active agent selected from the group consisting of sodium lauryl sulfate, sodium myristyl sulfate, hydrogenated coconut fatty acid monoglyceride monosodium sulfate, sodium dodecylbenzenesulfonate, 1,2-dihydroxypropanesulfonate, sodium, potassium or ethanolamine salt of N-lauryol, N-myristoyl, or N-palmitoylsarcosine, sucrose monolaurate, sucrose dilaurate, lactose fatty acid esters, lactitol fatty acid esters, malitol fatty acid esters, stearyl monoglyceride, polyoxyethylene sorbitan monolaurate, polyoxyethylene sorbitan monosterate, polyoxyethylene (10,20,40,60,80,100 mol) hardened castor oil, polymers of ethylene oxide and propylene oxide, polyoxyethylene-polyoxypropylene monolauryl ester; or 0 to 1% by weight of a sweetener selected from the group consisting of saccharin, stevioside, neohesperidyldihydrochalocone, glycyrrhizin, perillartine, thawmatin, asparatylpheylalanine methyl ester, p-methoxycinnamic aldehyde, lactose, fructose, and sodium cycliamate; or a preservative selected from the group consisting of p-hydroxymethylbenzoic acid, p-hydroxyethlbenzoic acid, p-hydroxybutyl benzoic acid, sodium benzoate, and lower fatty acid monoglyceride; or mixtures of said humectant, surface active agent, sweetener or preservative.

38. The composition as claimed in claim 22, wherein the amount of the l-menthol is 0:01 to 10% by weight of the composition.

39. The composition as claimed in claim 1, further comprising 0.0001 to 1% by weight in the composition of flavorings selected from the group consisting of carbone, anethole, eugenol, methyl salicylate, spearmint oil, wintergreen oil, sassafras oil, clove oil, eucalyptus oil, spice essential oil and spice oleoresin.

40. The composition as claimed in claim 1, wherein the pH is 6 to 8.

41. The composition as claimed in claim 1, further comprising materials selected from the group consisting of aminocaproic acid, tranexamic acid, dextranase, amylase, protease, mutanase, lysozyme, lytic enzyme, sodium monofluorophosphate, potassium monofluorophosphate, sodium fluoride, ammonium fluoride, and stannous fluoride, chlorhexidine hydrochloride, dihydrocholesterol, glycyrrehetic acid, chlorophyll, caropeptide, vitamins, anti-calculus agents, antibacterial agents, anti-plaque agents, and potassium nitrate.

42. The composition as claimed in claim 11, further comprising an oxalic acid compound excluding alumum oxalate.

43. The composition as claimed in claim 1, which is in the form of toothpaste, toothpowder, liquid ointment, gel ointment, mouthwash, dental floss or oral band.

44. In the art of occlusion of dentinal tubule orifices affected by hypersensitivity, the improvement which consists of the step of occluding said tubular orifice with an amount of an aluminum and a carboxylate composition effective to deposit around the tubular orifice and reduce the flow rate of the dentinal fluid that stimulates the nerve causing dentinal hypersensitivity, said method comprising:
applying the composition of claim 1 to an oral cavity of a subject.

* * * * *